United States Patent [19]

O'Grady

[11] Patent Number: 4,687,506
[45] Date of Patent: * Aug. 18, 1987

[54] AGRICULTURAL SULFONAMIDE

[75] Inventor: William R. O'Grady, Newark, Del.

[73] Assignee: E. I. Du Pont de Nemours and Company, Wilmington, Del.

[*] Notice: The portion of the term of this patent subsequent to Feb. 26, 1997 has been disclaimed.

[21] Appl. No.: 551,467

[22] Filed: Nov. 14, 1983

Related U.S. Application Data

[63] Continuation of Ser. No. 196,266, Oct. 22, 1980, abandoned, which is a continuation-in-part of Ser. No. 098,780, Nov. 30, 1979, abandoned.

[51] Int. Cl.$^4$ .................... A01B 43/54; C07D 239/48; C07D 401/12
[52] U.S. Cl. .......................................... 71/92; 71/93; 544/323; 544/324; 544/208; 544/209

[58] Field of Search ..................... 71/92; 544/323, 324

[56] References Cited

U.S. PATENT DOCUMENTS

| 4,190,432 | 2/1980 | Levitt | 71/93 |
| 4,214,890 | 7/1980 | Levitt | 71/90 |
| 4,394,506 | 7/1983 | Levitt | 544/321 |

FOREIGN PATENT DOCUMENTS 121788  9/1966  Netherlands.

Primary Examiner—Catherine L. Mills

[57] ABSTRACT

This invention relates to novel compounds of Formula I which are sulfonamides, agricultural compositions containing them and the method of using them as pre- and post-emergence herbicides and/or plant growth regulants.

20 Claims, No Drawings

AGRICULTURAL SULFONAMIDE

This application is a continuation of my copending application U.S. Ser. No. 196,266 filed Oct. 22, 1980, abandoned which in turn is a continuation-in-part of copending application U.S. Ser. No. 098,780 filed Nov. 30, 1979, now abandoned.

BACKGROUND OF THE INVENTION

Netherlands Pat. No. 121,788 claims herbicides such as.

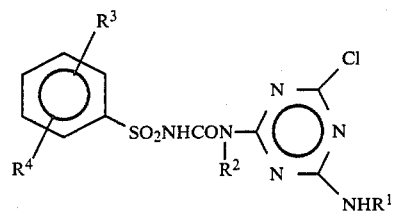

wherein
$R^1$ and $R^2 = C_1 - C_4$ alkyl; and
$R^3$ and $R^4 = H$, Cl or $C_1 - C_4$ alkyl.

In addition, U.S. Pat. No. 4,127,405 teaches herbicidal compounds such as those of the formula

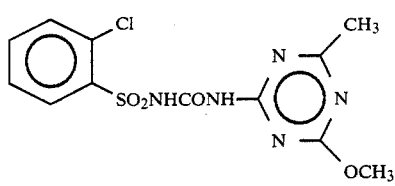

The presence of undesired vegetation causes substantial damage to useful crops, especially agricultural products that satisfy man's basic food and fiber needs, such as cotton, rice, corn, wheat, soybeans and the like. The current population explosion and concomitant world food and fiber shortage demand improvements in the efficiency of producing these crops. Preventing or minimizing the loss of a portion of such valuable crops by killing or inhibiting the growth of undesired vegtation is one way of improving this efficiency.

A wide variety of materials useful for killing or inhibiting (controlling) the growth of undesired vegetation is available; such materials are commonly referred to as herbicides. The need exists, however, for still more effective herbicides that destroy or control weeds without causing significant damage to useful crops.

SUMMARY OF THE INVENTION

According to this invention, there are provided novel compounds of Formula I and their agriculturally suitable salts and methods for using them as general or selective pre-emergence and post-emergence herbicides and/or plant growth regulators.

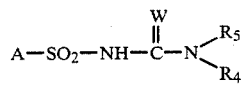

wherein
A is

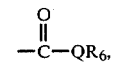

$R_1$ is

F, Cl, Br, $CH_3$, $OCH_3$, $NO_2$, $CF_3$, $SO_2NR_7R_8$, $S(O)_nR_8'$,

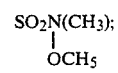

$OSO_2R_{10}$ and

$R_2$ is H, Cl, $CH_3$, $CF_3$, $NO_2$ or $OCH_3$;
$R_3$ is H, F, Cl, Br, $CH_3$, $OCH_3$, $NO_2$, $CO_2R_{11}$ or $S(O)_nR_{12}$;
$R_4$ is H or $CH_3$;
Q is O, S or $$-\underset{R_{13}}{\overset{|}{N}}-;$$

$R_6$ is $C_1-C_4$ alkyl, $C_3-C_4$ alkenyl, or $CH_3OCH_2CH_2$; when Q is O, then $R_6$ is also $ClCH_2CH_2$;
$R_{13}$ is H, $C_1-C_2$ alkyl, $OCH_3$ or $R_6$ and $R_{13}$ can be taken together to form $-CH_2CH_2CH_2CH_2-$ or $-CH_2CH_2O-CH_2CH_2-$;
$R_8'$ is $C_1-C_3$ alkyl;
$R_9$ is H or $C_1-C_4$ alkyl;
$R_{10}$ is $C_1-C_4$ alkyl or $CF_3$;
$R_{11}$ is $C_1-C_{14}$ alkyl;
$R_{12}$ is $C_1-C_3$ alkyl;
$R_7$, $R_8$ are independently $C_1-C_4$ alkyl provided that the total number of carbon atoms is less than or equal to five;
W is O or S;
n is 0, 1 or 2;
$R_5$ is

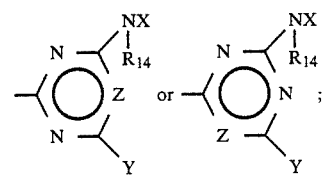

$R_{14}$ is H or $CH_3$;
Z is CH or N;
Y is F, Cl, Br, $C_1-C_2$ alkyl, $OCH_3$, $OCH_2CH_3$ and $CH_3OCH_2$;
X is H,

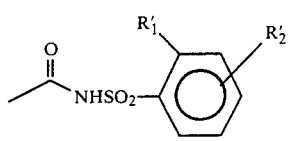

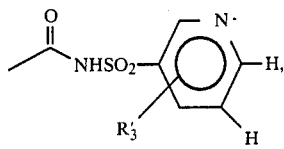

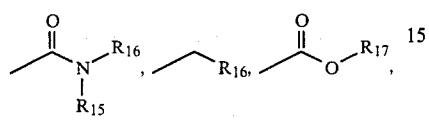

CH₃SO₂ or CF₃SO₂;
R₁' is

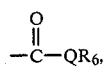

F, Cl, Br, CH₃, OCH₃, NO₂, CF₃, SO₂NR₇R₈, S(O)$_n$R₈',

OSO₂R₁₀, and

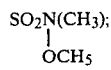

R₂' is H, Cl, CH₃, CF₃, NO₂ or OCH₃;
R₃' is H, F, Cl, Br, CH₃, OCH₃, NO₂, CO₂R₁₁ or S(O)$_n$R₁₂;
R₁₅ is H, C₁-C₄ alkyl, C₃-C₄ alkenyl or OCH₃;
R₁₆ is H, C₁-C₆ alkyl, phenyl, or phenyl optionally substituted with CF₃, F, NO₂, CN, 1-2Cl, 1-2Br, 1-2CH₃ or 1-2OCH₃;
R₁₇ is C₁-C₆ alkyl, phenyl or phenyl optionally substituted with CF₃, F, NO₂, CN, 1-2Cl, 1-2Br, 1-2CH₃ or 1-2OCH₃;
with the proviso that:
(1) when X is H or CH₃, then Y cannot be CH₃, OCH₃ or OCH₂CH₃;
(2) when Y is F, Cl or Br, then R₅ is

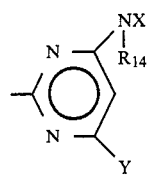

(3) when R₁₅ is OCH₃ then R₁₆ is CH₃;
(4) when R₁₃ is OCH₃, then R₆ is CH₃; and
their agriculturally suitable salts.

PREFERRED COMPOUNDS

Preferred for reasons of higher biological activity and/or lower cost and/or greater ease of synthesis are:

(1) Compounds of the generic scope in which W is oxygen and R₄ is hydrogen;
(2) Compounds of Preferred (1) in which R₁ and R₁' are

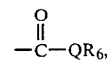

NO₂, Cl, SO₂NR₇R₈,

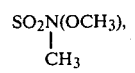

S(O)$_n$R₈' and OSO₂R₁₀;
(3) Compounds of Preferred (2) in which R₅ is

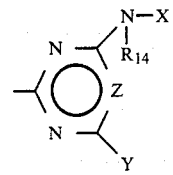

(4) Compounds of Preferred (3) in which R₁'=R₁, R₂'=R₂ and R₃'=R₃ and R₃ is in 2-position of the pyridine ring;
(5) Compounds of Preferred (4) in which R₁₅ is C₁-C₂ alkyl, CH₂—CH=CH₂, OCH₃ or H and R₁₆ is H, C₁-C₃ alkyl, phenyl or phenyl optionally substituted with CF₃, NO₂, 1-2Cl, CH₃ or OCH₃;
(6) Compounds of Preferred (5) in which R₁₇ is C₁-C₃ alkyl, phenyl or phenyl optionally substituted with Cl, Br, CH₃ or OCH₃;
(7) Compounds of Preferred (6) in which R₂ is H;
(8) Compounds of Preferred (7) in which R₆ is C₁-C₃ alkyl or CH₂CH=CH₂ and R₁₃ is CH₃; R₁ is NO₂, SO₂N(R₇,R₈)₂,

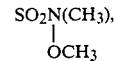

SO₂R₈', OSO₂CH₃ and R₃ is Cl, or SO₂CH₃; provided that the total number of carbons for (R₇,R₈) is ≦4;
(9) Compounds of Preferred (8) in which Z is CH;
(10) Compounds of Preferred (9) in which X is

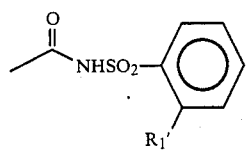

(11) Compounds of Preferred (9) in which X is

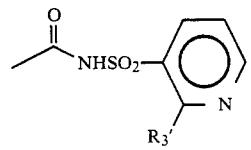

(12) Compounds of Preferred (9) in which X is H;
(13) Compounds of Preferred (9) in which X is

(14) Compounds of Preferred (9) in which X is

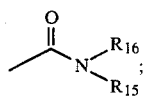

(15) Compounds of Preferred (9) in which X is

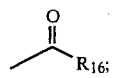

(16) Compounds of Preferred (9) in which X is $CH_3SO_2$;
(17) Compounds of Preferred (9) in which X is $CF_3SO_2$.
(18) Compounds of Preferred (13) in which $R_{15}$ is H, $C_1$–$C_3$ alkyl or $OCH_3$ and $R_{16}$ is H or $C_1$–$C_3$ alkyl.
(19) Compounds of Preferred (14) in which $R_{16}$ is $C_1$–$C_3$ alkyl.
(20) Compounds of Preferred (15) in which $R_{17}$ is $C_1$–$C_3$ alkyl.

Specifically Preferred for highest activity and/or lowest cost and/or greatest ease of synthesis are:

methyl 2-[[(4-amino-6-chloropyrimidin-2-yl)-aminocarbonyl]aminosulfonyl]benzoate;

dimethyl 2,2'-[6-chloropyrimidine-4,2-diyl-bis[-(aminocarbonyl)aminosulfonyl]]bis[benzoate];

N-[4-[[(2-chlorophenyl)sulfonylamino]carbonylamino]-6-methyl-1,3,5-triazin-2-yl]acetamide;

methyl 2-[[[4-(acetylamino)-6-methyl-1,3,5-triazin-2-yl]aminocarbonyl]aminosulfonyl]benzoate.

SYNTHESIS

The synthetic method for the preparation of compounds of Formula II, III, IV and V are shown in Equations 1A, B, C and D.

Compounds of Formulas II–V are conveniently prepared by reacting either one or two equivalents of an appropriately substituted benzenesulfonylisocyanate or pyridine sulfonyl isocyanate with an appropriately substituted diaminopyrimidine or triazine.

Equation 1

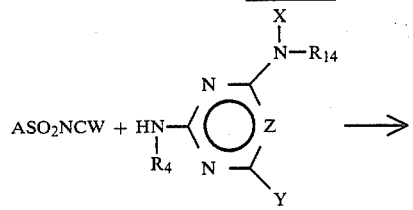

A

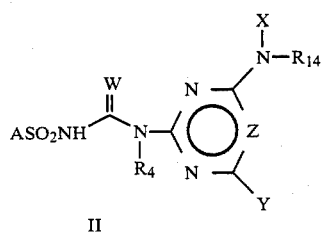

II

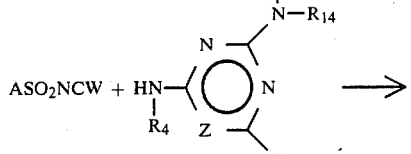

B

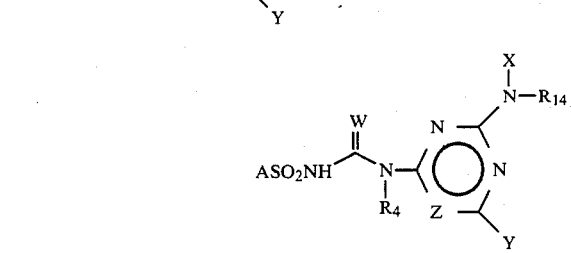

III

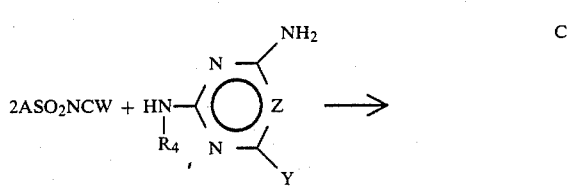

C

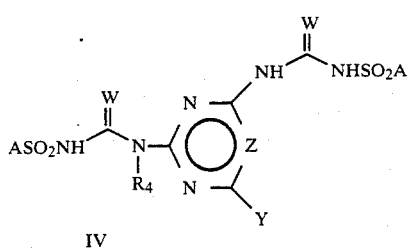

IV

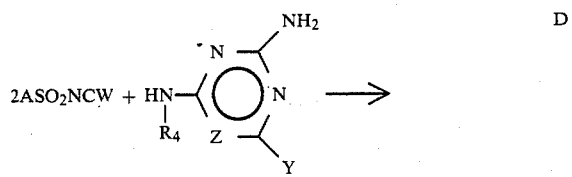

D

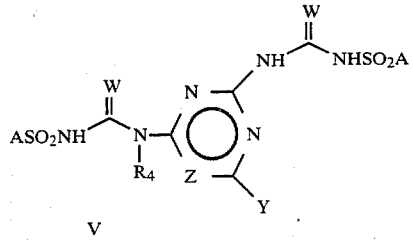

V

The reactions of Equation 1 are best carried out in inert aprotic organic solvents such as acetonitrile, tetrahydrofuran or methylene chloride. The reaction temperature can range from 25° C. to 81° C. The reaction time can range from 3–96 hours depending upon the reactivity of the aminoheterocycle. In some cases, the desired product crystallizes from the reaction medium and may be filtered. Other products which are soluble in the reaction medium are isolated by evaporation of the solvent, trituration of the residue with solvents such as ethyl ether, 1-chlorobutane or hexanes and filtration.

Other compounds in the scope of this invention are prepared as shown in Equation 2.

Equation 2

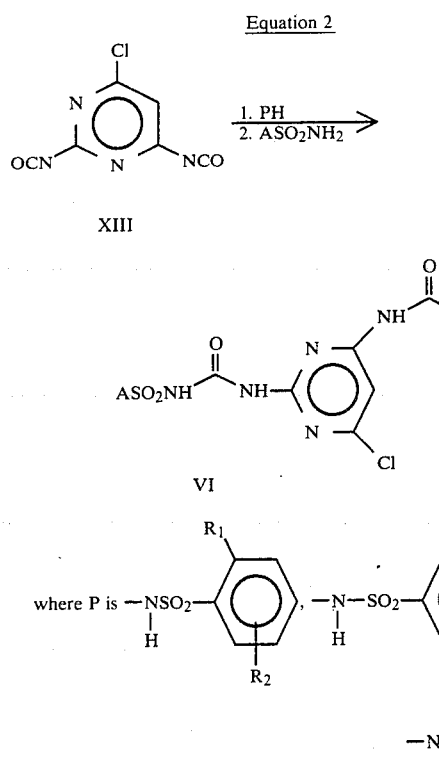

The intermediate 4-chloro-2,6-diisocyanatopyrimidine, XIII is prepared as described in Angew Chem. Int. Ed. Engl. 10, 402 (1971). Compounds of Formula VI may be prepared by sequential addition of one equivalent of a nucleophile defined as PH, followed by one equivalent of the appropriately substituted benzenesulfonamide, or pyridine sulfonamide to XIII.

The reaction of Equation 2 is best carried out in inert aprotic organic solvents such as acetonitrile, tetrahydrofuran or methylene chloride.

Another route to compounds of this invention is shown in Equation 3A.

Equation 3

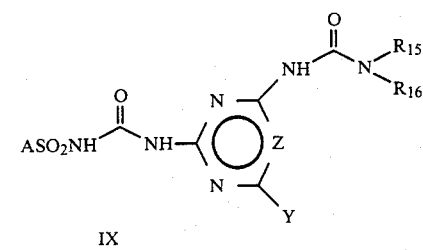

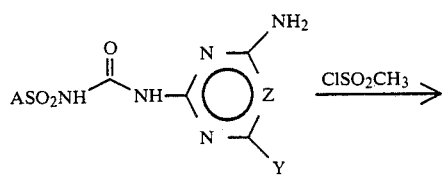

The synthetic method for the preparation of Formula VII is as described in Equation 3A. A mixture of the appropriately substituted XIV can be heated in acetic anhydride to give compounds of Formula VII.

Similarly, compounds of Formula VIII, IX, X, XI and XII can be prepared according to Equations 3B, 3C, 3D, 3E and 3F.

Equations 3B, C, D, E and F

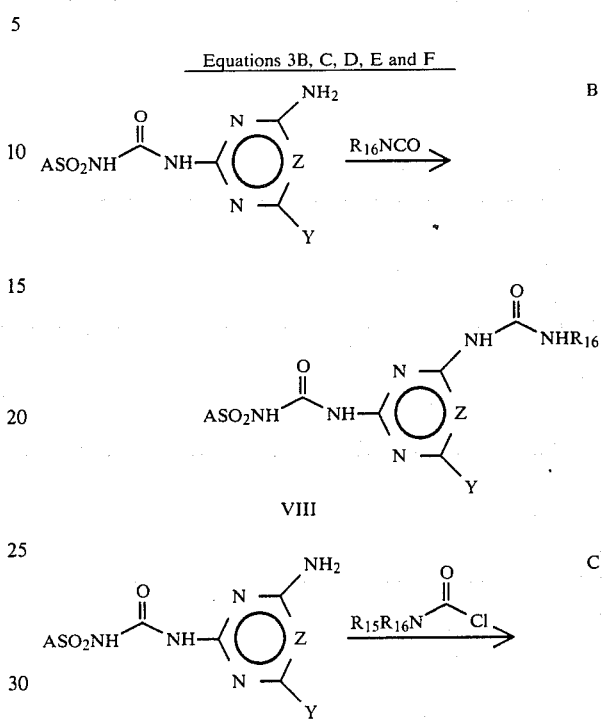

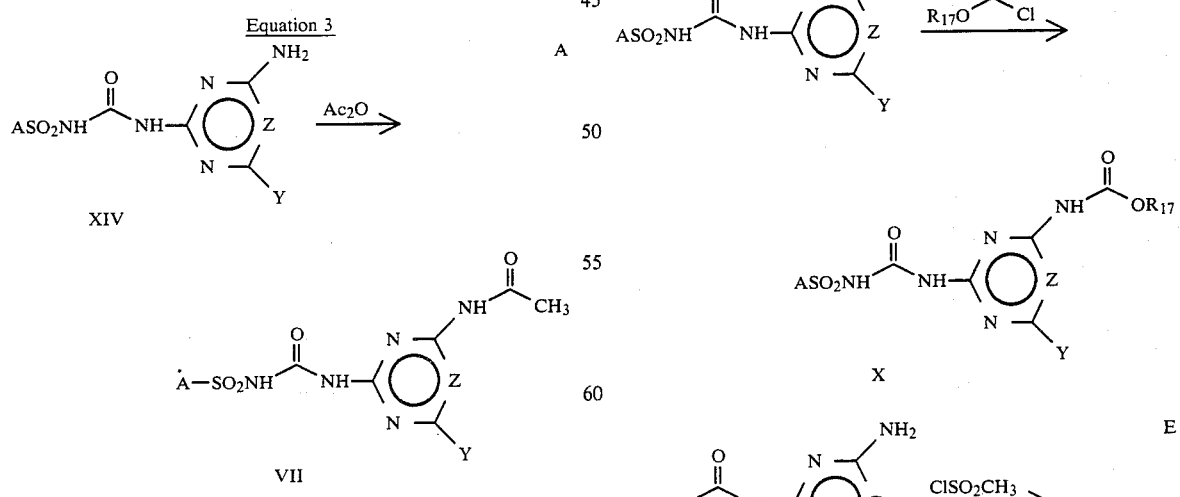

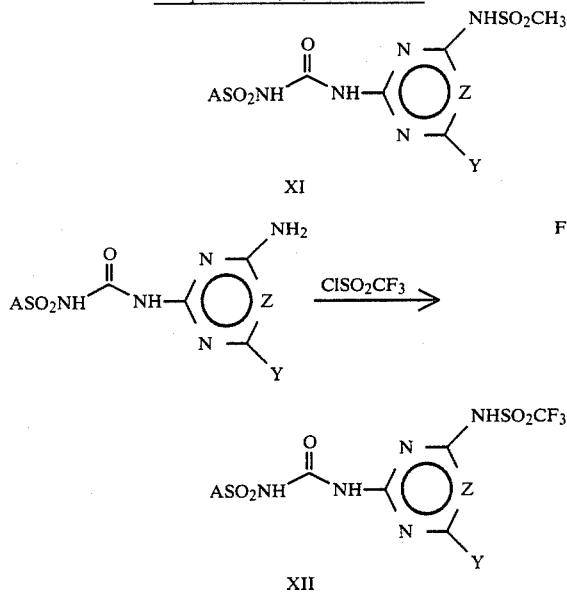

Starting materials and intermediates for compounds not otherwise described herein are disclosed in U.S. Pat. No. 4,127,408 and "The Chemistry of Heterocyclic Compounds, The Pyrimidines", Interscience Publishers, D. J. Brown, S. F. Mason (1962).

The compounds of this invention are further illustrated by the following examples.

EXAMPLE 1

2-{[(4-amino-6-chloropyrimidin-2-yl)aminocarbonyl-]aminosulfonyl}benzoic acid, methyl ester To a warmed mixture containing 1.4 g (0.01 mole) 2,4-diamino-6-chloropyrimidine in 50 ml acetonitrile is added 2.4 g (0.01 mole) 2-carbomethoxybenzenesulfonylisocyanate. The reaction mixture was stirred at room temperature for four days. The reaction mixture was filtered and the precipitate washed with ether. The filtered solid was air dried and purified in the following manner. To an aqueous suspension of the reaction mixture was added n-propylamine and the aqueous mixture filtered. The resultant clear solution was carefully acidified with concentrated HCl to pH=1–2. The mixture was filtered, washed with ether and air dried to yield a white solid, m.p. 170°–172° C. The infrared spectrums showed characteristic absorption bands at 1740, 1700 cm$^{-1}$. The NMR and mass spectral data are consistent for the desired product.

EXAMPLE 2

2,2'[6-chloropyrimidin-2,4-diylbis(aminocarbonyl-)aminosulfonyl]bis[benzoic acid], dimethyl ester To a warmed mixture containing 0.72 g (0.005 mole) 2,4-diamino-6-chloropyrimidine in 60 ml acetonitrile is added 4.3 g (0.018 mole) 2-carbomethoxybenzenesulfonylisocyanate. The reaction is heated to reflux temperature for four days. After cooling to room temperature, the resultant ppt. was filtered and dried to yield 0.8 g, m.p. 206°–210°. The infrared spectrum shows characteristic absorption bands at 1725, 1675 cm$^{-1}$.

Elemental analysis: Calc.: C, 42.14; H, 3.05; N, 13.40; Cl, 5.65; S, 10.23. Found: C, 42.2; H, 3.1; N, 14.2; Cl, 6.6; S, 10.3.

N-[4[2-Chlorophenyl-[sulfonylamino(carbonylamino)]]-2-methyl-1,3,5-triazin-2-yl]acetamide To 15 ml acetonitrile is added 1 g (0.006 mole) N-(4-amino-6-methyl-1,3,5-triazin-2-yl)acetamide and catalytic amount of dábco. To this suspension is added 1.8 g (0.008 mole) 2-chlorobenzenesulfonylisocyanate. The mixture is heated to 40° C. and is kept at 40° C. for 1 hour. The mixture is then cooled down to room temperature and is stirred at room temperature overnight. The solid is then collected by filtration, washed with acetonitrile, methylene chloride and n-butyl chloride, and dried to yield 2 g, m.p. 211°–213° C. The infrared spectrum shows characteristic absorption bands at 1655 cm$^{-1}$, 1700 cm$^{-1}$. NMR is consistent for the desired product.

Compounds of Tables I–VI can be prepared according to Equations 1–3, as previously described.

TABLE I

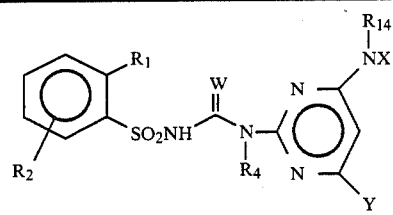

| $R_1$ | $R_2$ | $R_4$ | X | Y | W | $R_{14}$ |
|---|---|---|---|---|---|---|
| ![](OCH2CH2CH2CH3 ester) | H | H | H | Cl | O | H |
| ![](acetate ester) | 5-Cl | H | ![](benzoate NHSO2) | Cl | O | H |

TABLE I-continued
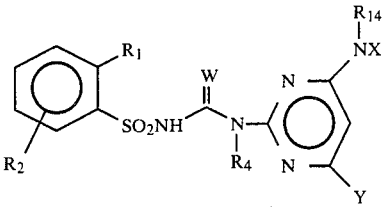
| R₁ | R₂ | R₄ | X | Y | W | R₁₄ |
|---|---|---|---|---|---|---|
| Cl | H | H | 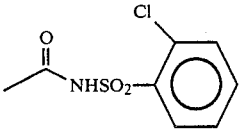 | Cl | S | H |
| CH₃ | 5-CH₃ | H | 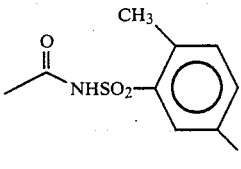 | Cl | O | H |
|  | H | H | 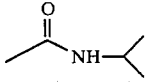 $\text{NH}_2$ | Cl | O | H |
|  | H | H | 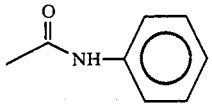 | OCH₃ | O | H |
|  | H | H | 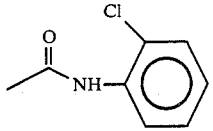 | CH₃ | O | H |
|  | H | H | 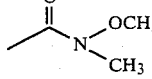 | Cl | O | H |
|  | H | H | 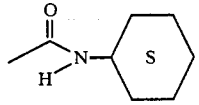 | Cl | O | H |
|  | H | H | 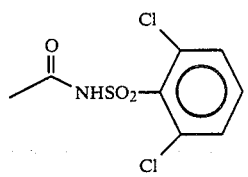 | Cl | O | H |
| Cl | 6-Cl | H | H | Cl | O | H |
| Cl | 6-Cl | H | 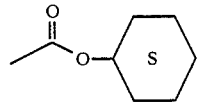 | Cl | O | H |
| Br | H | H |  | F | O | H |

TABLE I-continued
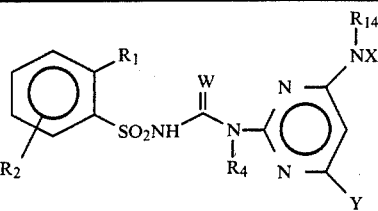
| R₁ | R₂ | R₄ | X | Y | W | R₁₄ |
|---|---|---|---|---|---|---|
| CH₃ | 5-CH₃ | H | 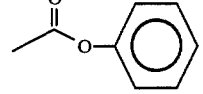 | Cl | O | H |
| SCH₃ | H | H | 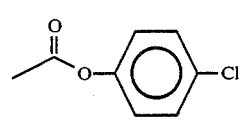 | Cl | O | H |
| SO₂CH₃ | H | H | 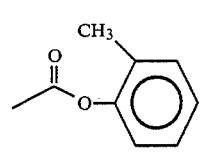 | Cl | O | H |
| NO₂ | H | H | $\overset{O}{\underset{}{\text{C}}}\text{CH}_3$ | Cl | O | H |
| CF₃ | H | H | 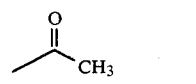 | Cl | O | H |
| SO₂N(CH₃)₂ | H | H | 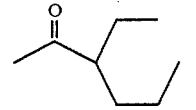 | Cl | O | H |
| 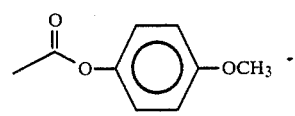 | H | H | 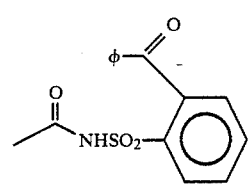 | Cl | O | H |
| 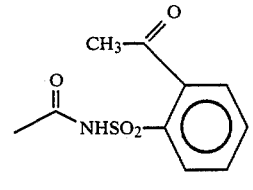 | H | H | 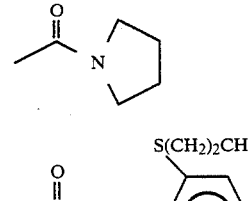 | Cl | O | H |
| 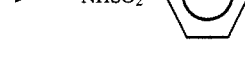 | H | H |  | Cl | O | H |
| SCH₂CH₂CH₃ | H | H |  | S(CH₂)₂CH₃ | CH₃ | O | H |

TABLE I-continued

| R₁ | R₂ | R₄ | X | Y | W | R₁₄ |
|---|---|---|---|---|---|---|
| SO₂(CH₂)₂CH₃ | H | H | CH₃(CH₂)₂O₂S-C(O)-NHSO₂-phenyl | CH₃ | O | H |
| SO₂N(CH₃)(CH₂)₃CH₃ | H | H | C(O)-phenyl | CH₃ | O | H |
| C(O)(CH₂)₃CH₃ | H | H | C(O)CH₃ | Cl | O | H |
| OSO₂CH₃ | H | H | (2-OSO₂CH₃-phenyl)-NHSO₂-C(O)- | Cl | O | H |
| OSO₂(CH₂)₃CH₃ | H | H | C(O)CH₃ | Cl | O | H |
| OSO₂CF₃ | H | H | C(O)CH₃ | Cl | O | H |
| SO₂N(CH₃)(OCH₃) | H | H | C(O)CH₃ | Cl | O | H |
| Cl | 5-CF₃ | H | C(O)CH₃ | Cl | O | H |
| Cl | 5-NO₂ | H | C(O)CH₃ | Cl | O | H |
| Cl | 6-OCH₃ | H | C(O)CH₃ | Cl | O | H |
| Cl | H | CH₃ | C(O)CH₃ | Cl | O | H |
| C(O)N(CH₃)₂ | H | H | C(O)CH₃ | Cl | O | H |
| C(O)NH-CH₂CH₃ | H | H | C(O)CH₃ | Cl | O | H |

TABLE I-continued

Structure: Ar-SO₂NH-C(W)-N(R₄)-pyrimidine with R₁, R₂ on phenyl; NXR₁₄ and Y on pyrimidine.

| R₁ | R₂ | R₄ | X | Y | W | R₁₄ |
|---|---|---|---|---|---|---|
| -C(O)N(CH₃)(OCH₃) | H | H | -C(O)CH₃ | Cl | O | H |
| OCH₃ | H | H | -C(O)OCH₃ | -CH₂CH₃ | O | H |
| Cl | H | H | H | -CH₂OCH₃ | O | H |
| -C(O)OCH₃ | H | H | -C(O)NHSO₂-(2-chloropyridin-3-yl) | Cl | O | H |
| -C(O)OCH₃ | H | H | -C(O)N(CH₃)₂ | Cl | O | H |
| -C(O)OCH₃ | H | H | -C(O)NH-CH₂-CH=CH₂ | Cl | O | H |
| -C(O)OCH₃ | H | H | -C(O)NH-CH₂CH₂-CH=CH₂ | Cl | O | H |
| Cl | H | H | -C(O)NH-(2,4-dimethoxyphenyl) | Cl | O | H |
| Cl | H | H | -C(O)NH-(2,4-dimethylphenyl) | Cl | O | H |
| Cl | H | H | -C(O)NH-(4-bromophenyl) | Cl | O | H |
| Cl | H | H | -C(O)O-(4-fluorophenyl) | Cl | O | H |
| Cl | H | H | -C(O)O-(4-nitrophenyl) | Cl | O | H |

TABLE I-continued

| R₁ | R₂ | R₄ | X | Y | W | R₁₄ |
|---|---|---|---|---|---|---|
| Cl | H | H | (acetyl-O-phenyl-CN) | Cl | O | H |
| Cl | H | H | (acetyl-O-2,4-dichlorophenyl) | Cl | O | H |
| Cl | H | H | (acetyl-O-3,4-dibromophenyl) | Cl | O | H |
| Cl | H | H | (acetyl-O-2,4-dibromophenyl) | Cl | O | H |
| Cl | H | H | (acetyl-O-4-CF₃-phenyl) | Cl | O | H |
| Cl | H | H | H | Cl | O | H |
| Cl | H | H | H | Cl | O | CH₃ |
| Br | H | H | H | Cl | O | CH₃ |
| F | H | H | H | Cl | O | CH₃ |

TABLE II

| R₁ | R₂ | R₄ | X | Y | W | R₁₄ |
|---|---|---|---|---|---|---|
| CH₃O(C=O)– | H | H | (acetyl-NHSO₂-phenyl-2-CO₂Me) | OCH₃ | O | H |
| CH₃O(C=O)– | H | H | (acetyl-NHSO₂-phenyl-2-Cl) | OCH₃ | O | H |

TABLE II-continued
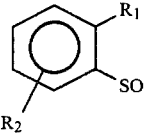
| R₁ | R₂ | R₄ | X | Y | W | R₁₄ |
|---|---|---|---|---|---|---|
| 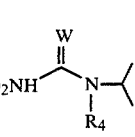 | H | H | 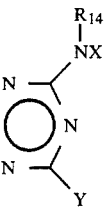 | OCH₃ | O | H |
| 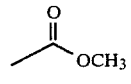 | H | H | 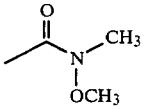 | OCH₃ | O | H |
| 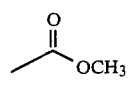 | H | H | 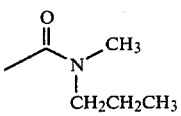 | OCH₃ | O | H |
| 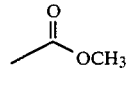 | H | H | 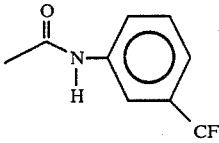 | OCH₃ | O | H |
| 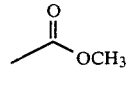 | H | H | 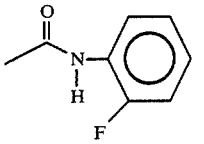 | OCH₃ | O | H |
| 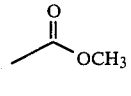 | H | H | 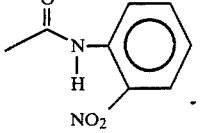 | OCH₃ | O | H |
| 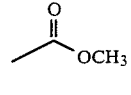 | H | H | 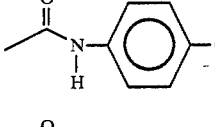 | OCH₃ | O | H |
| 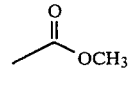 | H | H | 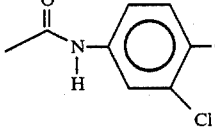 | OCH₃ | O | H |
| 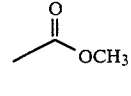 | H | H | 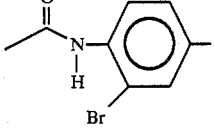 | OCH₃ | O | H |
| 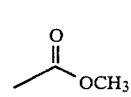 | H | H | 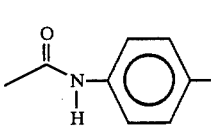 | OCH₃ | O | H |

TABLE II-continued

Structure: 
```
         R1
          \
       [benzene ring]
          /           W
        R2   SO2NH—C—N(R4)—[triazine with N-NXR14 at top, Y at bottom]
```

| R1 | R2 | R4 | X | Y | W | R14 |
|---|---|---|---|---|---|---|
| CH3-C(=O)-O-CH(CH3)CH2CH3 (sec-butyl acetate group) | H | H | CH3-C(=O)-NHSO2-C6H4-C(=O)-O- (2-acylsulfamoylphenyl ester) | OCH3 | O | H |
| F | H | H | 2-F-C6H4-SO2-NH-C(=O)-CH2- | OCH3 | O | H |
| Cl | 6-Cl | H | 2,6-Cl2-C6H3-SO2-NH-C(=O)-CH2- | OCH3 | O | H |
| Br | H | H | 2-Br-C6H4-SO2-NH-C(=O)-CH2- | OCH3 | O | H |
| CH3 | 5-CH3 | H | 2,5-(CH3)2-C6H3-SO2-NH-C(=O)-CH2- | OCH3 | O | H |
| —SO2N(CH3)2 | H | H | 2-[(CH3)2NSO2]-C6H4-SO2-NH-C(=O)-CH2- | OCH3 | O | H |
| CH3-C(=O)-OCH3 | H | H | 2-(CH3O2C)-C6H4-SO2-NH-C(=O)-CH2- | OCH3 | O | H |
| CH3-C(=O)-OCH3 | H | H | 2-(CH3O2C)-C6H4-SO2-NH-C(=O)-CH2- | OCH3 | O | H |

TABLE II-continued

[Structure: benzene ring with R1 (ortho), R2 (para), -SO2NH-C(W)-N(R4)- linked to triazine ring with NX(R14), and Y substituent]

| R1 | R2 | R4 | X | Y | W | R14 |
|---|---|---|---|---|---|---|
| -C(O)OCH3 | H | H | -C(O)-NHSO2-C6H4-(CH3O2C) | OCH3 | O | H |
| -C(O)OCH3 | H | H | -C(O)-NHSO2-C6H4-(CH3O2C) | CH3 | O | H |
| -C(O)OCH3 | H | H | -C(O)-NHSO2-C6H4-(CH3O2C) | OCH3 | O | H |
| -C(O)OCH3 | H | H | -C(O)-NHSO2-C6H4-(CH3O2C) | -CH2CH3 | O | H |
| -C(O)OCH3 | H | H | -C(O)-NHSO2-C6H4-(CH3O2C) | -OCH2CH3 | O | H |
| OCH3 | H | H | -C(O)-NHSO2-C6H4-(CH3O) | OCH3 | O | H |
| SCH3 | H | H | -C(O)-NHSO2-C6H4-(CH3S) | OCH3 | O | H |
| SO2CH3 | H | H | -C(O)-NHSO2-C6H4-(CH3SO2) | OCH3 | O | H |
| NO2 | H | H | -C(O)-NHSO2-C6H4-(O2N) | OCH3 | O | H |

TABLE II-continued

[Structure: phenyl ring with R1 (ortho) and R2 (meta) substituents, connected via SO2NH-C(=W)-N(R4)- to a triazine ring bearing N(R14)X group and Y substituent]

| R₁ | R₂ | R₄ | X | Y | W | R₁₄ |
|---|---|---|---|---|---|---|
| CF₃ | H | H | -C(=O)-NHSO₂-(2-CF₃-phenyl) | OCH₃ | O | H |
| -C(=O)OCH₃ | H | H | H | | S | H |
| Cl | H | H | -C(=O)-NHSO₂-(2-Cl-phenyl) | OCH₃ | O | H |
| Cl | H | H | -C(=O)-NHSO₂-(2-Cl-phenyl) | OCH₂CH₃ | O | H |
| Cl | H | H | -C(=O)-NHSO₂-(2-Cl-phenyl) | CH₃ | O | H |

TABLE III

[Structure: phenyl ring with R1, R2 substituents, connected via SO2NH-C(=W)-N(R4)- to a pyrimidine ring bearing N(R14)X at 2-position and Y at other position]

| R₁ | R₂ | R₄ | X | Y | W | R₁₄ |
|---|---|---|---|---|---|---|
| -C(=O)OCH₃ | H | H | H | Cl | O | H |
| Cl | H | H | H | Cl | O | H |
| -SO₂N(CH₃)₂ | H | H | H | Cl | O | H |
| -C(=O)OCH₃ | H | H | -C(=O)-NHSO₂-(2-CO₂CH₃-phenyl) | CH₃ | O | H |
| -C(=O)OCH₃ | H | H | -C(=O)-NHSO₂-(2-CO₂CH₃-phenyl) | Cl | O | H |
| Cl | H | H | -C(=O)-NHSO₂-(2-Cl-phenyl) | Cl | O | H |

TABLE IV

Structure: pyridine-SO₂NH-C(W)-N(R₄)-pyrimidine with substituents R₃ (on pyridine), X and R₁₄ (on one pyrimidine N), Y (on pyrimidine).

| R₃ | R₄ | X | Y | W | R₁₄ |
|---|---|---|---|---|---|
| 2-Cl | H | -C(O)-NHSO₂-(2-chloropyridin-3-yl) | Cl | O | H |
| 2-Cl | H | -C(O)-NHSO₂-(2-CO₂CH₃-phenyl) | Cl | O | H |
| 2-Cl | H | -C(O)-N(H)CH₃ | Cl | O | H |
| 2-Cl | H | -C(O)CH₃ | Cl | O | H |
| 2-Cl | H | -C(O)-phenyl | Cl | O | H |
| 2-Cl | H | -C(O)-(4-chlorophenyl) | Cl | O | H |
| 2-Cl | H | -C(O)-OCH₃ | Cl | O | H |
| 2-Cl | H | -C(O)-O-phenyl | Cl | O | H |
| 2-Cl | H | -C(O)-O-(4-fluorophenyl) | Cl | O | H |
| 2-Cl | H | -C(O)-NH-phenyl | Cl | O | H |
| 2-Cl | CH₃ | -C(O)CH₃ | Cl | O | H |
| 2-Cl | H | -C(O)CH₃ | Cl | O | CH₃ |

TABLE IV-continued $$\text{H-pyridine(R}_3\text{)-SO}_2\text{NH-C(=W)-N(R}_4\text{)-pyrimidine[N(X)(R}_{14}\text{), Y]}$$

| R$_3$ | R$_4$ | X | Y | W | R$_{14}$ |
|---|---|---|---|---|---|
| 2-Br | H | -C(=O)-NHSO$_2$-(2-Br-phenyl) | Cl | O | H |
| 2-F | H | -C(=O)-NHCH$_3$ | Cl | O | H |
| 4-Cl | CH$_3$ | -C(=O)-CH$_3$ | Cl | O | H |
| 2-CH$_3$ | H | -C(=O)-CH$_3$ | Cl | O | H |
| 2-OCH$_3$ | H | -C(=O)-NHCH$_3$ | Cl | O | H |
| 2-NO$_2$ | H | -C(=O)-OCH$_3$ | Cl | O | H |
| 2-C(=O)OCH$_3$ | H | -C(=O)-OCH$_3$ | Cl | O | H |
| 2-C(=O)O-iso-C$_4$H$_9$ | H | -C(=O)-NHCH$_3$ | Cl | O | H |
| 2-SCH$_3$ | H | -C(=O)-NHCH$_3$ | Cl | O | H |
| 2-SO$_2$CH$_3$ | H | -C(=O)-OCH$_3$ | Cl | O | H |
| 2-SCH$_2$CH$_2$CH$_3$ | H | -C(=O)-OCH$_3$ | Cl | O | H |
| H | H | -C(=O)-OCH$_3$ | Cl | O | H |

TABLE V

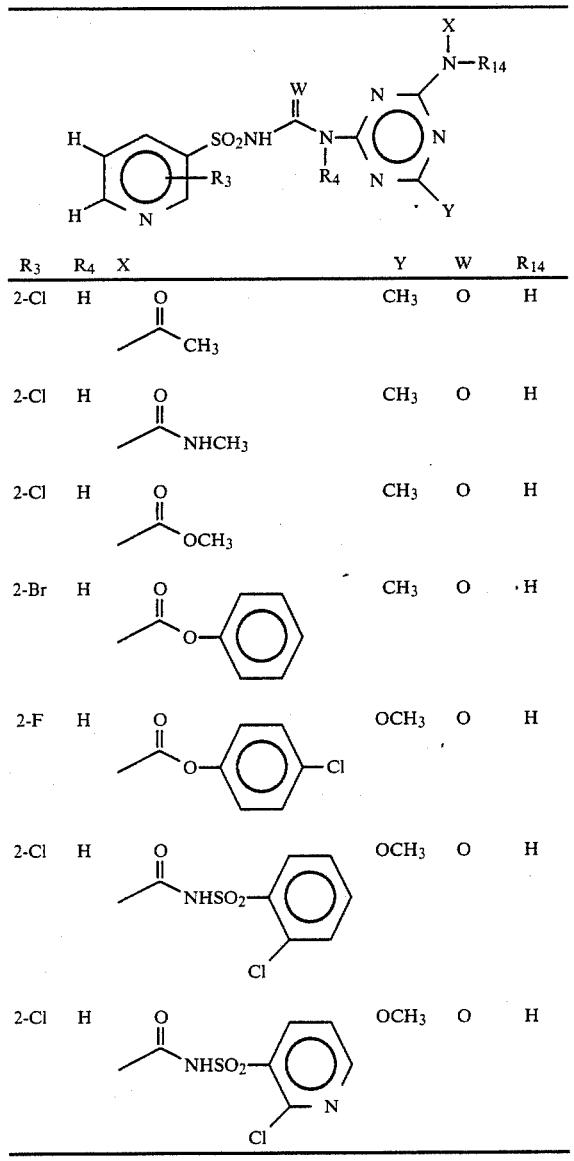

| R3 | R4 | X | Y | W | R14 |
|---|---|---|---|---|---|
| 2-Cl | H | -C(O)CH3 | CH3 | O | H |
| 2-Cl | H | -C(O)NHCH3 | CH3 | O | H |
| 2-Cl | H | -C(O)OCH3 | CH3 | O | H |
| 2-Br | H | -C(O)O-phenyl | CH3 | O | H |
| 2-F | H | -C(O)O-(4-Cl-phenyl) | OCH3 | O | H |
| 2-Cl | H | -C(O)NHSO2-(2-Cl-phenyl) | OCH3 | O | H |
| 2-Cl | H | -C(O)NHSO2-(2-Cl-pyridyl) | OCH3 | O | H |

TABLE VI

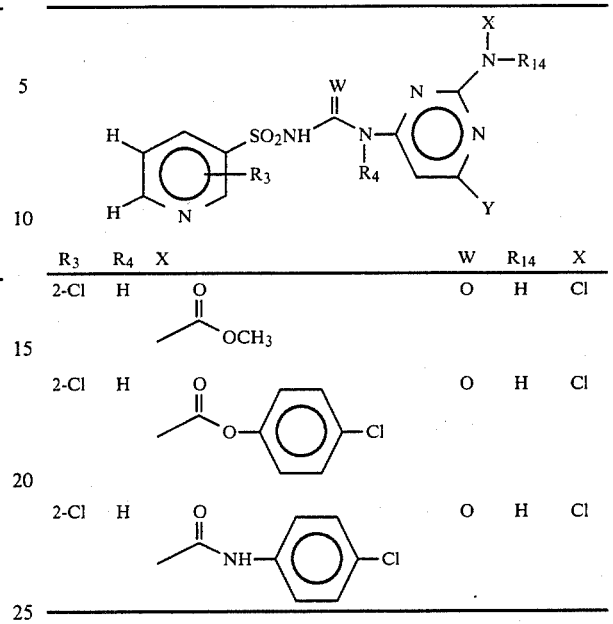

| R3 | R4 | X | W | R14 | X |
|---|---|---|---|---|---|
| 2-Cl | H | -C(O)NHSO2-(2-Cl-phenyl) | O | H | Cl |
| 2-Cl | H | -C(O)NHCH3 | O | H | Cl |

TABLE VI-continued

| R3 | R4 | X | W | R14 | X |
|---|---|---|---|---|---|
| 2-Cl | H | -C(O)OCH3 | O | H | Cl |
| 2-Cl | H | -C(O)O-(4-Cl-phenyl) | O | H | Cl |
| 2-Cl | H | -C(O)NH-(4-Cl-phenyl) | O | H | Cl |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VII

| | Weight % | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp. Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 4th Ed., McGraw-Hill, New York, 1963, pp. 8-59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Examples 8, 12, 15, 39, 41, 52, 53, 132, 138-140, 162-164, 166, 167 and 169-182.

H. Gysin and E. Knusli, U.S. Pat. No. 2,891,855, June 23, 1959, Col. 3, line 66 through Col. 5, line 17 and Examples 1-4.

G. C. Klingman, "Weed Control as a Science", John Wiley & Sons, Inc., New York, 1961, pp. 81-96.

J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 4

Wettable Powder

Dimethyl 2,2'-[6-chloropyrimidine-2,4-diylbis[(aminocarbonyl)aminosulfonyl]]bis[benzoate]: 50%;
sodium alkylnaphthalenesulfonate: 2%;
low viscosity methyl cellulose: 2%;
diatomaceous earth: 46%.

The ingredients are blended, coarsely hammer-milled and then air-milled to produce particles of active essentially all below 10 microns in diameter. The product is reblended before packaging.

EXAMPLE 5

Granule wettable powder of Example 4: 5%;
attapulgite granules: 95%;
(U.S.S. 20-40 mesh; 0.84-0.42 mm).

A slurry of wettable powder containing ≈25% solids is sprayed on the surface of attapulgite granules in a double-cone blender. The granules are dried and packaged.

EXAMPLE 6

Oil Suspension

Dimethyl 2,2'-[6-chloropyrimidine-2,4-diylbis[(aminocarbonyl)aminosulfonyl]]bis[benzoate]: 25%;
polyoxyethylene sorbitol hexaoleate: 5%;
highly aliphatic hydrocarbon oil: 70%.

The ingredients are ground together in a sand mill until the solid particles have been reduced to under about 5 microns. The resulting suspension may be applied directly, but preferably after being extended with oils or emulsified in water.

EXAMPLE 7

Low Strength Granule

Dimethyl 2,2'-[6-chloropyrimidine-2,4-diylbis[(aminocarbonyl)aminosulfonyl]]bis[benzoate]: 0.1%;
attapulgite granules: 99.9%;
(U.S.S. 20-40 mesh).

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 8

Wettable Powder

Methyl 2-[[(4-amino-6-chloropyrimidin-2-yl)aminocarbonyl]aminosulfonyl]benzoate: 80%;
sodium alkylnaphthalenesulfonate: 2%;
sodium ligninsulfonate: 2%;
synthetic amorphous silica: 3%;
kaolinite: 13%.

The ingredients are blended, hammer-milled until the solids are essentially under 50 microns, reblended and packaged.

EXAMPLE 9

Extruded Pellet

Methyl 2-[[(4-amino-6-chloropyrimidin-2-yl)aminocarbonyl]aminosulfonyl]benzoate: 25%;
anhydrous sodium sulfate: 10%;
crude calcium ligninsulfonate: 5%;
sodium alkylnaphthalenesulfonate: 1%;
calcium/magnesium bentonite: 59%.

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Wettable Powder

Methyl 2-[[(4-amino-6-chloropyrimidin-2-yl)aminocarbonyl]aminosulfonyl]benzoate: 20%;
sodium alkylnaphthalenesulfonate: 4%;
sodium ligninsulfonate: 4%;
low viscosity methyl cellulose: 3%;
attapulgite: 69%.

The ingredients are thoroughly blended. After grinding in a hammer mill to produce particles essentially all below 100 microns, the material is reblended and sifted through a U.S.S. No. 50 sieve (0.3 mm opening) and packaged.

EXAMPLE 11

High Strength Concentrate

Methyl 2-[[(4-amino-6-chloropyrimidin-2-yl)aminocarbonyl]aminosulfonyl]benzoate: 99%;
silica aerogel: 0.5%;
synthetic amorphous silica: 0.5%.

The ingredients are blended and ground in a hammer mill to produce a material essentially all passing a U.S.S. No. 50 screen (0.3 mm opening). The concentrate may be formulated further if necessary.

EXAMPLE 12

Aqueous Suspension

Methyl 2-[[(4-amino-6-chloropyrimidin-2-yl)aminocarbonyl]aminosulfonyl]benzoate: 40%;
Polyacrylic acid thickener: 0.3%;
Dodecylphenol polyethylene glycol ether: 0.5%;
Disodium phosphate: 1%;
Monosodium phosphate: 0.5%;
Polyvinyl alcohol: 1.0%;
Water: 56.7%.

The ingredients are blended and ground together in a sand mill to produce particles essentially all under 5 microns in size.

EXAMPLE 13

Granule

Methyl 2-[[(4-amino-6-chloropyrimidin-2-yl)aminocarbonyl]aminosulfonyl]benzoate: 80%;
wetting agent: 1%;
crude ligninsulfonate salt (containing 5-20% of the natural sugars): 10%;
attapulgite clay: 9%.

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1910-149 microns), and packaged for use.

UTILITY

The compounds of Formula I are useful as herbicides. They may be applied either pre- or post-emergence for the control of undesired vegetation in noncrop areas or for selective weed control in certain crops, e.g., wheat. Some of these compounds are useful for the pre- and/or post-emergence control of nutsedge. By properly selecting rate and time of application, compounds of this invention may be used to modify plant growth beneficially.

The precise amount of the compound of Formula I to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. The lower rates of the range will generally be selected for lighter soils, for selective weed control in crops, or in situations where maximum persistence is not necessary. Some of the compounds of Formula I can be used at very low rates for plant growth modification, but higher rates may also be useful, depending on factors such as crop being treated, timing of treatment, etc.

The compounds of Formula I may be combined with other herbicides and are particularly useful in combination with 3-(3,4-dichlorophenyl)-1,1-dimethylurea, the triazines, such as 2-chloro-4-(ethylamino)-6-(isopropylamino)-s-triazine, the uracils such as 5-bromo-3-sec-butyl-6-methyl uracil, N-(phosphonomethyl)glycine, 3-cyclohexyl-1-methyl-6-dimethylamino-s-triazine-2,4(1H,3H)-dione, N,N-dimethyl-2,2-diphenylacetamide, 2,4-dichlorophenoxyacetic acid (and closely related compounds), 4-chloro-2-butynyl-3-chlorophenylcarbamate (Carbyne ®), diisopropylthiolcarbamic acid, ester with 2,3-dichloroallyl alcohol (Avadex ®), diisopropylthiolcarbamic acid, S-(2,3,3-trichlorallyl)ester (Avadex ® BW), ethyl-N-benzoyl-N-(3,4-dichlorophenyl)-2-aminopropionate (Suffix ®), 1,2-dimethyl-3,5-diphenylpyrazolium methyl-sulfate (Avenge ®), methyl 2-[4-(2,4-dichlorophenoxy)-phenoxy]-propanoate (Hoelon ®), 4-amino-6-tert-butyl-3-(methylthio)-1,2,4-triazin-5(4H)-one (Lexone ®), 3-(3,4-dichlorophenyl)-1-methoxy-1-methylurea (Lorox ®), 3-isopropyl-1H-2,1,3-benzothiodiazin-(4)-3H-one 2,2-dioxide, α,α,α-trifluoro-2,6-dinitro-N,N-dipropyl-p-toluidine, 1,1'-dimethyl-4,4'-bipyridinium ion, monosodium methanearsonate, 2-chloro-2',6'-diethyl-(methoxymethyl)acetanilide, and 1,1-dimethyl-3-(α,α,α-trifluoro-m-tolyl)urea (Cotoran ®).

The activity of these compounds was discovered in a number of greenhouse tests. The test is described and the data resulting from them are shown below.

TEST PROCEDURE A

Seeds of crabgrass (Digitaria spp.), barnyardgrass (Echinochloa crusgalli), wild oats (Avena fatua), Cassia tora, morningglory (Ipomoea spp.) cocklebur (Xanthium spp.), sorghum, corn, soybean, rice, wheat and nutsedge, tubers were planted in a growth medium and treated pre-emergence with the chemicals dissolved in a non-phytotoxic solvent. At the same time, cotton having five leaves (including cotyledonary ones), bush beans with the second trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three-five leaves were sprayed. Treated plants and controls were maintained in a greenhouse for sixteen days, then all species were compared to controls and visually rated for response to treatment. The ratings are based on a numerical scale extending from 0=no injury, to 10=complete kill. The accompanying descriptive symbols have the following meanings:

G=growth retardation;
C=chlorosis/necrosis;

D=defoliation;
E=emergence inhibition;
H=formative effects; and
U=unusual pigmentation.

The data for compounds tested by this procedure are in Table A.

grass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Da-*

TABLE A

| | kg/ha | |
|---|---|---|
| | 0.4 | 0.4 |
| POST-EMERGENCE | | |
| BUSHBEAN | 8D,7G,6Y | 9C |
| COTTON | 3C,3H,6G | 5C,9G |
| MORNINGGLORY | 4C,9G | 10C |
| COCKLEBUR | 2C,9G | 9C |
| CASSIA | 3C,8G | 6C,9G |
| NUTSEDGE | 9G | 9C |
| CRABGRASS | 2C,7G | 2C,9H |
| BARNYARDGRASS | 9C | 10C |
| WILD OATS | 2C,9G | 3C,9G |
| WHEAT | 2C,3G | 3C,8G |
| CORN | 3C,9H | 6U,9G |
| SOYBEAN | 2C,3H,9G | 4C,9G |
| RICE | — | 5C,9G |
| SORGHUM | 4C,9G | 10C |
| PRE-EMERGENCE | | |
| MORNINGGLORY | 8G | 9G |
| COCKLEBUR | 9G | 9H |
| CASSIA | 7G | 5C,9G |
| NUTSEDGE | 10E | 10E |
| CRABGRASS | 1C,3G | 6G |
| BARNYARDGRASS | 2C,9H | 9H |
| WILD OATS | 1C,8G | 3C,9H |
| WHEAT | 7G | 2C,9H |
| CORN | 1C,9G | 5C,9G |
| SOYBEAN | 6H | 9H |
| RICE | 10E | 10E |
| SORGHUM | 6C,9G | 3C,9H |

TEST PROCEDURE B

Two plastic bulb pans were filled with fertilized and limited Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallistura stramonium). A 12.5 cm diameter plastic pot was also filled with prepared soil and planted with rice and wheat. Another 12.5 cm pot was planted with sugarbeets. The above four containers were treated preemergence with several test compounds within the scope of the invention.

Twenty-eight days after treatment, the plants were evaluated and visually rated for response to the chemical treatments utilizing the rating system described previously for Test A. The data are summarized in Table B.

TABLE B

PRE-EMERGENCE ON FALLSINGTON SILT LOAM

| Rate kg/ha | Crab-grass | Barn-yard-grass | Sorghum | Wild Oats | John-son-grass | Dal-lis-grass | Giant foxtail | Ky. blue-grass | Cheat-grass | Sugar-beets | Corn | Mustard |
|---|---|---|---|---|---|---|---|---|---|---|---|---|
| 0.03 | 5G | 6G,3H | 10C | 3G,2C | 9G,6C | 5G | — | 6G,3C | 8G,7C | 7G,7C | 7G,7H | 10C |
| 0.06 | 7G | 8G,5H | 10C | 6G,3C | 9G,9C | 6G | 5G | 7G,6C | 10C | 10C | 8G,5C | 10C |
| 0.25 | 8G,3C | 10C | 10C | 10C | 10C | 9G,9C | 10C | 9G,9C | 10C | 8G,8C | 10C | 10C |
| | | | | | | | | | | | | |
| 0.03 | 0 | 0 | 0 | 0 | 0 | 0 | 0 | 0 | 0 | 0 | 0 | 0 |
| 0.12 | 0 | 0 | 7G,3H | 0 | 7G,3H. | 0 | — | 3G | 3G | 0 | 2G | 8G,3C |
| | | | | | | | | | | | | |
| 0.06 | 0 | 0 | 3H | 0 | 0 | — | 0 | 0 | 0 | 0 | 0 | 8G,8C |
| 0.25 | 0 | 0 | 5G,3H | 5G | 2G | — | — | 0 | 4G | 4G | 2G | 8G,9C |

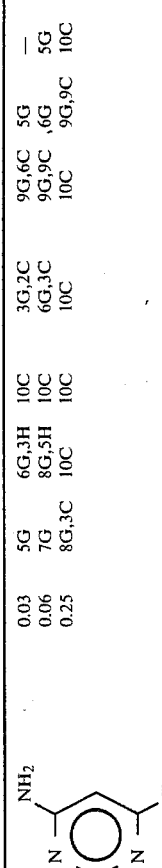

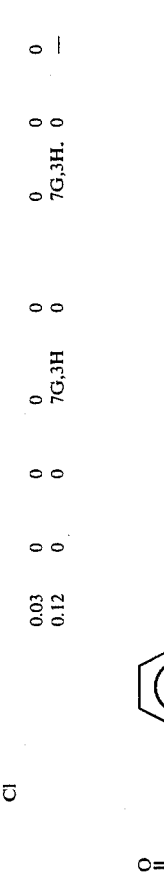

 73%

+

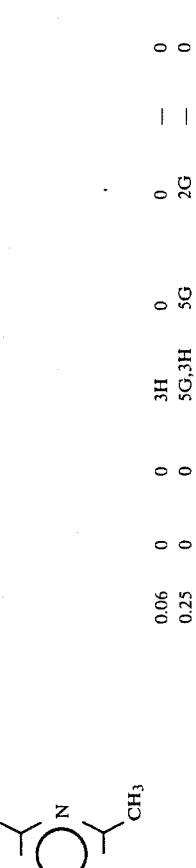 27%

| Rate kg/ha | Cock-lebur | Pigweed | Nut-sedge | Cotton | Morn-ing-glory | Cassia | Tea-weed | Vel-vetleaf | Jimsonweed | Soybean | Rice | Wheat |
|---|---|---|---|---|---|---|---|---|---|---|---|---|

TABLE B-continued
PRE-EMERGENCE ON FALLSINGTON SILT LOAM

| Compound | Rate | | | | | | | | | | | | |
|---|---|---|---|---|---|---|---|---|---|---|---|---|---|
| ![structure with NH2, Cl, SO2-NH-C(=O)-NH, COOCH3] | 0.03<br>0.06<br>0.25 | —<br>7G,5H<br>7G,5H | —<br>—<br>— | 10E<br>10E<br>10E | 0<br>2H<br>8G,5H | 3G<br>6G<br>7G,5H | 5G<br>8G,8C<br>8G,9C | 0<br>8E<br>10E | 7G,5H<br>10C<br>10C | 7G,5H<br>0<br>5G,6C | 7G,5H<br>8G,5H<br>8G,8H | 10E<br>10E<br>10E | 0<br>4G<br>8G,8C |
| ![structure with Cl, SO2-NH-C(=O)-NH, COOCH3] | 0.03<br>0.12 | 0<br>0 | —<br>— | 2G<br>8G | 0<br>2G | 0<br>0 | 0<br>0 | —<br>— | 0<br>4G,3H | 0<br>0 | 0<br>0 | | |
| ![structure with NHCCH3, CH3, SO2-NH-C(=O)-NH, phenyl] 73%<br>+<br>![structure with NHCCH3, CH3, H2N] 27% | 0.06<br>0.25 | 0<br>0 | 0<br>0 | 0<br>0 | 0<br>3G | 3G,2H<br>7G,5H | 0<br>0 | 0<br>0 | 2H<br>4G,3H | 0<br>0 | 3H<br>2G,2H | 4G<br>7G,8C | 0<br>6G,5C |

TEST PROCEDURE C

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiforum*) and ripgut brome (*Bromus rigidus*). The other pan was planted with seeds of Russian thistle (*Salsola kali*) tansy mustard (*Descuraina pinnata*), smartweed (*Polygonum pensylvanicum*), tumble mustard (*Sisymbrium altissium*), kochia (*Kochia scoparia*), shepherd's purse (*Capsella bursa-pastoris*), *Matricaria inodora*, black night shade (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1-15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table C.

TABLE C

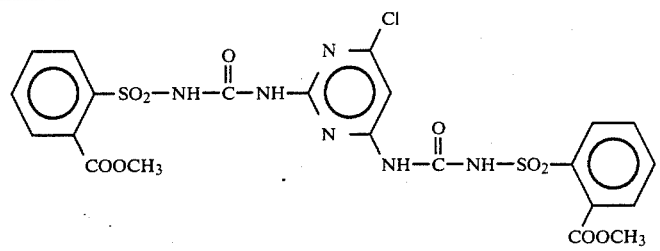

| | Rate kg/ha | |
|---|---|---|
| | 0.06 Post-emergence | 0.06 Pre-emergence |
| wheat | 0 | 0 |
| barley | 0 | 0 |
| wild oats | 0 | 1G |
| downy brome | 2C,3G | 1C,1G |
| cheatgrass | 3C,6G | 6C,7G |
| blackgrass | 3C,7G | 1C,3G |
| annual bluegrass | 5G | 5G |
| green foxtail | 1C,2G | 1G |
| quackgrass | 2G | 1C,2G |
| Italian ryegrass | 3G | 3C,4G |
| ripgut brome | 0 | 0 |
| Russian thistle | 2G | 2C,3G |
| tansy mustard | 3C,6G | 8C,8G |
| smartweed | — | — |
| jimhill mustard | 7C,8G | 10C |
| Kochia | 2G | 3C,4G |
| shepherd's purse | 8C,8G | 5C,4G |
| false chamomile | 3C,4G | 3C,3G |
| black nightshade | 3C,2G | 0 |
| yellow rocket | 7C,8G | 6C,5G |
| wild mustard | 10C | 8C,8G |
| wild buckwheat | 3C,3G | 3C,4G |

TEST PROCEDURE D

Purple nutsedge (*Cyperus rotundus*) tubers were planted about 2 cm deep in Fallsington silt loam soil contained in 10 cm diameter plastic pots. Five tubers were planted in each pot. Conmpounds of this invention were dissolved in an non-phytotoxic diluent and sprayed at 560 l/ha in four methods of application: soil surface, tuber/soil, soil incorporated, and post-emergence. The soil surface spray consisted of spraying the compound on the surface of the firmed covering soil. The tuber/soil spray consisted of spraying the compound on exposed tubers and subtending soil before adding the untreated covering soil. Soil incorporated treatment consisted in mixing the compound with the covering soil before using it to cover the tubers. The post-emergence treatment was sprayed on nutsedge foliage and the surrounding soil surface when nutsedge had emerged and grown to a height of about 12 cm. Pots receiving the post-emergence treatments were placed directly in the greenhouse. Pots receiving the other treatments were misted with about 0.3 cm water before being transferred to the greenhouse. Response ratings assessed after four weeks are recorded in Table D based on the same rating system as described in procedure A.

TABLE D

Nutsedge Control

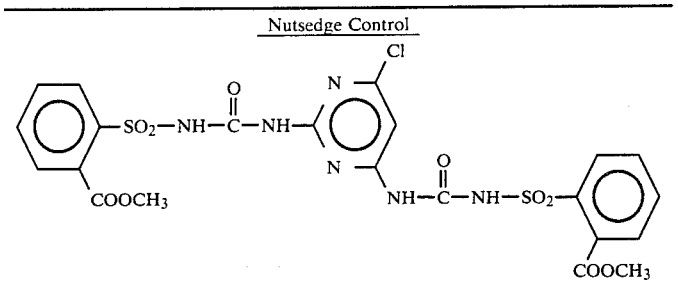

| Rate kg/ha | Response Rating (after 4 wks) | | | |
|---|---|---|---|---|
| | Preemerg. Soil Surface | Tuber Spray | Soil Incorp. | Postemerg. |
| 0.008 | 2G | 2G | 2G | 2G |
| 0.031 | 2G | 2G | 3G | 4G |
| 0.125 | 5E,8G | 10E | 8E,8G | 3C,7G |

TEST PROCEDURE E

Twenty-five cm diameter plastic pots filled with Fallsington silt loam were planted to soybeans, cotton, alfalfa, corn, rice, wheat, sorghum, velvetleaf (*Abutilon theophrasti*), sesbania (*Sesbania exaltata*), cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were spayed overall with the test chemicals dissolved in a nonphytotoxic solvent. Fourteen days after treatment, all species were compared to untreated controls and visually rated for response to treatment. The rating system was as described previously for Test A. the data are presented in Table E.

TABLE E

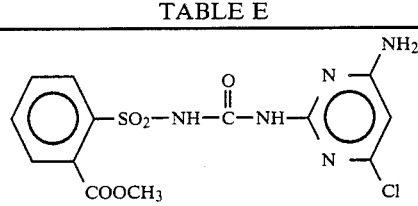

| | Rate kg/ha | | | |
|---|---|---|---|---|
| | 0.25 | 0.06 | 0.015 | 0.007 |
| Soybeans | 10C | 10C | 10C | 9G,6C |
| Velvetleaf | — | — | — | 9G,5C |
| Sesbania | 10C | 10C | — | 8G,4C |
| Cassia | 10G,9C | 10G,7C | 10G,7C | 6G,2C |
| Cotton | 8G,3C | 6G,3C | 6G,3C | 6G,3C |
| Morningglory | 10C | 10G,7C | 8G,3C | 6G,2C |
| Alfalfa | 10C | 10C | 9C | 7G,2C |
| Jimsonweed | — | — | — | 0 |
| Cocklebur | 9C | — | 7G,3C | 8G,5C |
| Corn | 9G,5G | 9G,5G | 9G,7H | 4G,4H |
| Crabgrass | 9G,4C | 9G | 1G | 0 |
| Rice | 9G,4C | 9G,3C | 7G,3C | 7G,2C |
| Nutsedge | 9G,3C | 7G,1C | 7G | 8G,3C |
| Barnyardgrass | 10G,6C | 9G,5C | 9G,5C | 7G,1C |
| Wheat | 7G,3C | 7G,2C | 2G | 0 |
| Giant Foxtail | — | — | — | 8G,3C |
| Wild Oats | 10G,6C | 9G,4C | 8G,2C | 4G |
| Sorghum | 10G,8C | 9G,6C | 9G,4C | 9G,2C |

What is claimed is:
1. A compound selected from

$$A-SO_2-NH-\overset{W}{\underset{\parallel}{C}}-N\overset{R_5}{\underset{R_{r}}{\diagdown}} \quad [I]$$

and agriculturally suitable salts thereof, wherein:

A is

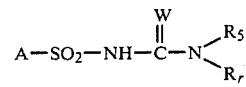

$R_1$ is

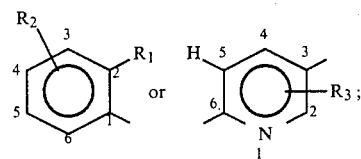

F, Cl, Br, $CH_3$, $OCH_3$, $NO_2$, $CF_3$, $SO_2NR_7R_8$, $S(O)_nR_8'$,

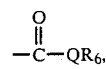

$OSO_2R_{10}$ or

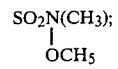

$R_2$ is H, Cl, $CH_3$, $CF_3$, $NO_2$ or $OCH_3$;
$R_3$ is F, Cl, Br, $CH_3$, $OCH_3$, or $S(O)_nR_{12}$;
$R_4$ is H or $CH_3$;
Q is O, S or

$R_6$ is $C_1$-$C_4$ alkyl, $C_3$-$C_4$ alkenyl, $CH_3OCH_2CH_2$;
when Q is O, then $R_6$ is also $ClCH_2CH_2$;
$R_{13}$ is H, $C_1$-$C_2$ alkyl, $OCH_3$ or $R_6$ and $R_{13}$ can be taken together to form $-CH_2CH_2CH_2CH_2-$ or $-CH_2CH_2O-CH_2CH_2-$; and when $R_{13}$ is $OCH_3$, then $R_6$ is $CH_3$;

$R_8'$ is $C_1$-$C_3$ alkyl;
$R_9$ is H or $C_1$-$C_4$ alkyl;
$R_{10}$ is $C_1$-$C_4$ alkyl or $CF_3$;
$R_{12}$ is $C_1$-$C_3$ alkyl;
$R_7$, $R_8$ are independently $C_1$-$C_4$ alkyl provided that the total number of carbon atoms is less than or equal to five;
W is O or S;
n is 0, 1 or 2;
$R_5$ is

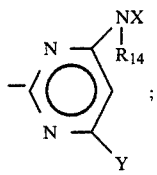

$R_{14}$ is H or $CH_3$;
Y is F, Cl, Br;
X is H, or

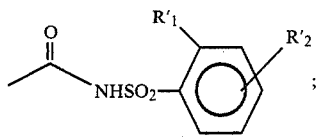

$R_1'$ is

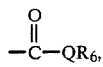

F, Cl, Br, $CH_3$, $OCH_3$, $NO_2$, $CF_3$, $SO_2NR_7R_8$, $S(O)_nR_8'$,

$OSO_2R_{10}$, or

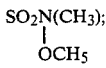

and
$R_2'$ is H, Cl, $CH_3$, $CF_3$, $NO_2$ or $OCH_3$.

2. A compound of claim 1 in which W is oxygen and $R_4$ is hydrogen.

3. A compound of claim 2 in which $R_1$ and $R_1'$ are

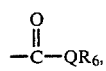

$NO_2$, Cl, $SO_2NR_7R_8$,

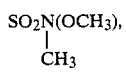

$S(O)_nR_8'$ or $OSO_2R_{10}$.

4. A compound of claim 3 in which $R_1' = R_1$ and $R_2' = R_2$.

5. A compound of claim 4 in which $R_2$ is H.

6. A compound of claim 5 in which $R_6$ is $C_1$-$C_3$ alkyl or $CH_2CH=CH_2$ and $R_{13}$ is $CH_3$; $R_1$ is $NO_2$, $SO_2N(R_7,R_8)_2$,

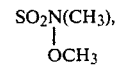

$SO_2R_8'$, $OSO_2CH_3$ and $R_3$ is Cl, or $SO_2CH_3$; provided that the total number of carbons for $(R_7,R_8)$ is $\leq 4$.

7. A compound of claim 5 in which X is

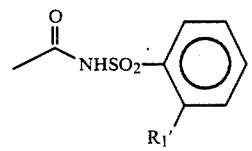

8. A compound of claim 2 in which X is H.

9. The compound of claim 1, methyl 2-[[(4-amino-6-chloropyrimidin-2-yl)-aminocarbonyl]aminosulfonyl]-benzoate.

10. The compound of claim 1, dimethyl 2,2'-[6-chloropyrimidine-4,2-diyl-bis[(aminocarbonyl)aminosulfonyl]]bis[benzoate].

11. A composition suitable for controlling the growth of undesired vegetation which comprises an effective amount of a compound of claim 1 and at least one of the following: surfactant, solid or liquid diluent.

12. A composition suitable for controlling the growth of undesired vegetation which comprises an effective amount of a compound of claim 2 and at least one of the following: surfactant, solid or liquid diluent.

13. A composition suitable for controlling the growth of undesired vegetation which comprises an effective amount of a compound of claim 3 and at least one of the following: surfactant, solid or liquid diluent.

14. A composition suitable for controlling the growth of undesired vegetation which comprises an effective amount of a compound of claim 4 and at least one of the following: surfactant, solid or liquid diluent.

15. A composition suitable for controlling the growth of undesired vegetation which comprises an effective amount of a compound of claim 5 and at least one of the following: surfactant, solid or liquid diluent.

16. A method for controlling the growth of undesired vegetation which comprises applying to the locus to be protected an effective amount of a compound of claim 1.

17. A method for controlling the growth of undesired vegetation which comprises applying to the locus to be protected an effective amount of a compound of claim 2.

18. A method for controlling the growth of undesired vegetation which comprises applying to the locus to be protected an effective amount of a compound of claim 3.

19. A method for controlling the growth of undesired vegetation which comprises applying to the locus to be protected an effective amount of a compound of claim 4.

20. A method for controlling the growth of undesired vegetation which comprises applying to the locus to be protected an effective amount of a compound of claim 5.

* * * * *

UNITED STATES PATENT AND TRADEMARK OFFICE
CERTIFICATE OF CORRECTION

PATENT NO. : 4,687,506
DATED : August 18, 1987
INVENTOR(S) : William Robert O'Grady It is certified that error appears in the above—identified patent and that said Letters Patent is hereby corrected as shown below:

In the Specification, at the top of Column 2, the structure on the right should appear as:

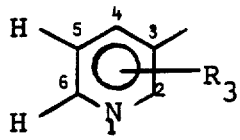

In the Claims, Claim 1, Column 48, the formula at lines 20 to 25 should appear as:

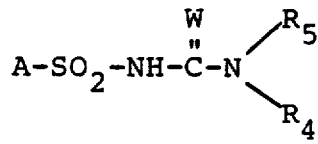

In Claim 1, Column 48, lines 30 to 35, the structure on the right should appear as:

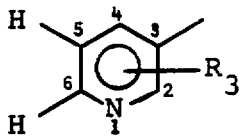

Signed and Sealed this

Twenty-sixth Day of April, 1988

Attest:

DONALD J. QUIGG

Attesting Officer

Commissioner of Patents and Trademarks